US011229380B2

(12) United States Patent
Dadashi et al.

(10) Patent No.: US 11,229,380 B2
(45) Date of Patent: Jan. 25, 2022

(54) METHOD FOR CHARACTERISING A GAIT (71) Applicants: Universite Paris Descartes, Paris (FR); Centre National de la Recherche Scientifique (CNRS), Paris (FR); Ecole Normale Superieure De Cachan, Cachan (FR); Etat Français—Ministére de la Défense—Direction centrale du service de santé des armées, Clamart (FR); Univ Paris XIII Paris-Nord Villetaneuse, Villetaneuse (FR)

(72) Inventors: Robert Dadashi, Strasbourg (FR); Thomas Moreau, Saint Paul En Chablais (FR); Charles Truong, Ezanville (FR); Catherine Vidal, Paris (FR); Alain Yelnik, Malakoff (FR); Rémi Barrois-Muller, Paris (FR); Nicolas Vayatis, Paris (FR); Laurent Oudre, Paris (FR); Pierre Paul Vidal, Paris (FR); Damien Ricard, Paris (FR)

(73) Assignees: Universite Paris Descartes; Centre National de la Recherche Scientifique (CNRS); Ecole Normale Superieure De Cachan; Etat Français—Ministére de la Défense—Direction centrale du service de santé des armées; Univ Paris XIII Paris-Nord Villetaneuse

( * ) Notice: Subject to any disclaimer, the term of this patent is extended or adjusted under 35 U.S.C. 154(b) by 345 days.

(21) Appl. No.: 15/750,309

(22) PCT Filed: Aug. 5, 2016

(86) PCT No.: PCT/EP2016/068796
§ 371 (c)(1),
(2) Date: Feb. 5, 2018

(87) PCT Pub. No.: WO2017/021545
PCT Pub. Date: Feb. 9, 2017

(65) Prior Publication Data
US 2018/0220936 A1    Aug. 9, 2018

(30) Foreign Application Priority Data

Aug. 6, 2015 (FR) ...................................... 1557582
Apr. 20, 2016 (EP) ...................................... 16020149

(51) Int. Cl.
*A61B 5/11* (2006.01)
*A61B 5/00* (2006.01)
*G01C 22/00* (2006.01)

(52) U.S. Cl.
CPC ............ *A61B 5/112* (2013.01); *A61B 5/6829* (2013.01); *A61B 5/7246* (2013.01); *A61B 5/6831* (2013.01);
(Continued)

(58) Field of Classification Search
None
See application file for complete search history.

(56) References Cited

U.S. PATENT DOCUMENTS

2006/0135883 A1* 6/2006 Jonsson ................ A61F 2/6607
600/546
2007/0021689 A1 1/2007 Stergiou et al.
(Continued)

FOREIGN PATENT DOCUMENTS

EP    2439492 A1    4/2012

OTHER PUBLICATIONS

French Search Report for FR1557582 dated Jun. 13, 2016.
International Search Report for PCT/EP2016/08796 dated Nov. 14, 2016.

*Primary Examiner* — Etsub D Berhanu

*Assistant Examiner* — Aurelie H Tu (74) *Attorney, Agent, or Firm* — Lerner, David, Littenberg, Krumholz & Mentlik, LLP (57) ABSTRACT

A method is provided for characterising a gait comprising steps of: receiving a signal measuring the movement of a target subject measured beforehand; comparing (204) at least one section of the measuring signal with a plurality of reference signals, the plurality of reference signals comprising at least one movement signal measured beforehand on a reference subject different from the target subject, each comparison of the measuring signal with a reference signal producing a similarity coefficient representative of a probability of similarity between the compared signals; and selecting (208) at least one local maximum of interest among the similarity coefficients produced, wherein the plurality of reference signals comprises at least one movement signal measured beforehand on a reference subject afflicted with a gait disorder, and at least one movement signal measured beforehand on a healthy reference object.

6 Claims, 4 Drawing Sheets

(52) U.S. Cl.
CPC .... *A61B 2562/0219* (2013.01); *G01C 22/006* (2013.01)

(56) References Cited

U.S. PATENT DOCUMENTS

| | | |
|---|---|---|
| 2011/0218463 A1 | 9/2011 | Hodgins et al. |
| 2012/0101411 A1* | 4/2012 | Hausdorff ............ A61B 5/6831 600/595 |
| 2013/0090881 A1 | 4/2013 | Janardhanan et al. |
| 2014/0159911 A1* | 6/2014 | Gray .................... A61B 5/0024 340/870.01 |
| 2016/0038060 A1* | 2/2016 | Kitamura ............... A61B 5/112 600/595 |

* cited by examiner

METHOD FOR CHARACTERISING A GAIT

CROSS REFERENCE TO RELATED APPLICATIONS

The present application is a national phase entry under 35 U.S.C. § 371 of International Application No. PCT/EP2016/068796 filed Aug. 5, 2016, published in French, which claims priority from French Patent Application No. 1557582 filed Aug. 6, 2015, and European Patent Application No. 16020149.7 filed Apr. 20, 2016, all of which are incorporated herein by reference.

GENERAL FIELD

The present invention relates to a method and a system for characterizing a person's gait.

PRIOR ART

Those methods aimed at characterizing gait of a person are of two types: methods for simple counting of steps, and methods for detection of steps, more complex as their aim is to determine precise characteristic instants of the step, such as the instant when the heel strikes the ground.

The majority of the known methods for detecting steps is based on a succession of ad hoc processing steps applied to a motion signal measured on a target subject.

Pan-Tomkins preprocessing is known for example, described in the article "A real-time QRS detection algorithm", by J. Pan and W. J Tompkins. This preprocessing comprises passband filtering, derivation, squaring, integration and peak search applied to the motion signal measured on the target subject.

A major disadvantage of these methods is that they require calibration of many parameters (sizes of filters, values of thresholds, criteria of selection of peaks, etc . . . ) which are often difficult to estimate or learn and are often selected empirically. Also, these methods are based on a very strong a priori on the form a step must have, clearly limiting their efficacy on target subjects whereof the step is of non-conventional form, for example people suffering from gait disorder.

SUMMARY OF THE INVENTION

An aim of the invention is to characterize gait of a subject without as such requiring a preliminary calibration step. This aim can include the fact of detecting steps or determining an information characteristic of the subject's gait.

Another aim of the invention is to be able to implement a method for characterizing gait which can function both on subjects afflicted by gait disorders and healthy subjects.

It is therefore proposed according to a first aspect of the invention a method for characterizing gait comprising steps of:
  receiving a signal for measuring motion of a previously measured target subject,
  comparing at least one portion of the measuring signal with a plurality of reference signals, the plurality of reference signals comprising at least one motion signal previously measured on a reference subject different to the target subject, each comparison of the measuring signal with a reference signal producing a similarity coefficient representative of a similarity probability between the compared signals,
  selecting at least one local maximum of interest among the similarity coefficients produced.

The plurality of reference signals comprises:
  at least one motion signal previously measured on a subject afflicted by a gait disorder, and
  at least one motion signal previously measured on a healthy reference subject.

The method for characterizing gait proposed hereinabove can be completed by means of the following features taken singly or else in combination when this is technically possible.

The method can comprise an identification step, in the measuring signal, of at least one marker instant characteristic of a step of the target subject, as a function of the reference signal from which the selected local maximum of interest has been produced.

The method can comprise a counting step of the number of selected local maximum of interest corresponding to a given reference signal, each reference signal being associated with an information characteristic of the corresponding reference subject.

The method can comprise a step of counting the number of local maximum of interest linked to each class of reference signals, each class of reference signals having been generated from information characteristic of the reference subjects.

At least one reference signal can be compared to several portions of the measuring signal temporarily shifted relative to each other, so as to produce an ordered sequence of similarity coefficients according to the temporary positions of the portions of the measuring signal; a similarity coefficient of a sequence is then selected as local maximum as a function of the result of a comparison between the value of the coefficient with the value of the coefficient which precedes it in the sequence, and of the result of comparison between the value of the coefficient with the value of the coefficient which follows it in the same sequence.

Each reference signal comprising at least one predetermined marker instant and characteristic of a step of a reference subject, at least one reference signal can be compared to several portions of the measuring signal temporarily shifted relative to each other, and the marker instant characteristic of a step of the target subject can be identified from the predetermined marker instant of the reference signal from which the selected local maximum of interest has been produced.

A local maximum may not be selected when it has a value less than a predetermined threshold.

The local maxima can be selected by decreasing order of value of the similarity coefficients.

A local maximum may not be selected when the portion of the measured signal, from which it has been produced, temporarily overlaps another portion of the measured signal from which an already selected local maximum has been produced. Such overlapping accelerates the search for local maxima and consequently reduces the implementation time of the method for characterizing gait.

The method can comprise calculation of a ratio between dimensional characteristics of the two compared signals. In this case, the identification step is not implemented for a local maximum produced from compared signals whereof the calculated dimension ratio exceeds a predetermined threshold.

The dimensional characteristics can be amplitudes or variances of the compared signals.

The comparison step can comprise correlation producing a Pearson linear coefficient, the similarity coefficient depending on the absolute value of the Pearson linear coefficient.

The plurality of reference signals can comprise reference signals of different durations.

The measuring signal can be a signal representative of the motion of a foot of the target subject.

The measuring signal can be or depend on at least the following signals:
- an acceleration signal of the target subject in a direction normal to the ground, and/or
- an acceleration signal of the target subject in a direction normal to an upper surface of a foot of the target subject, and/or
- an angular speed signal about an axis of rotation of a foot of the target.

The method can comprise acquisition of the measuring signal by at least one motion sensor attached to the target subject.

At least one reference signal can be acquired during a walking sequence comprising walking in a straight line of at least 5 meters by a reference subject.

According to a second aspect, a system for characterizing gait is further proposed, comprising:
- a receiving interface configured for receiving an acceleration measuring signal of a target subject, and
- at least one processor configured for:
  - comparing the measuring signal with a plurality of reference signals, the plurality of reference signals comprising at least one acceleration signal previously measured on a reference subject different to the target subject, each comparison of the measuring signal with a reference signal producing a similarity coefficient representative of a similarity probability between the compared signals,
  - selecting at least one local maximum among the similarity coefficients produced,
wherein the plurality of reference signals comprises:
- at least one motion signal previously measured on a reference subject afflicted by a gait disorder, and
- at least one motion signal previously measured on a healthy reference subject.

The system, according to this second aspect, can further comprise at least one motion sensor adapted to provide the measuring signal to the receiving interface.

This system can further comprise a memory in which the plurality of reference signals is stored.

According to a third aspect of the invention, a method of diagnosis and/or of prognosis of gait disorder of a target subject is further proposed, comprising implementing a method for characterizing gait according to the first aspect of the invention, the signal for measuring motion of the target subject having been previously measured.

DESCRIPTION OF THE FIGURES

In the figures, identical elements are designated by identical reference numerals.

DETAILED DESCRIPTION

Figure 1:
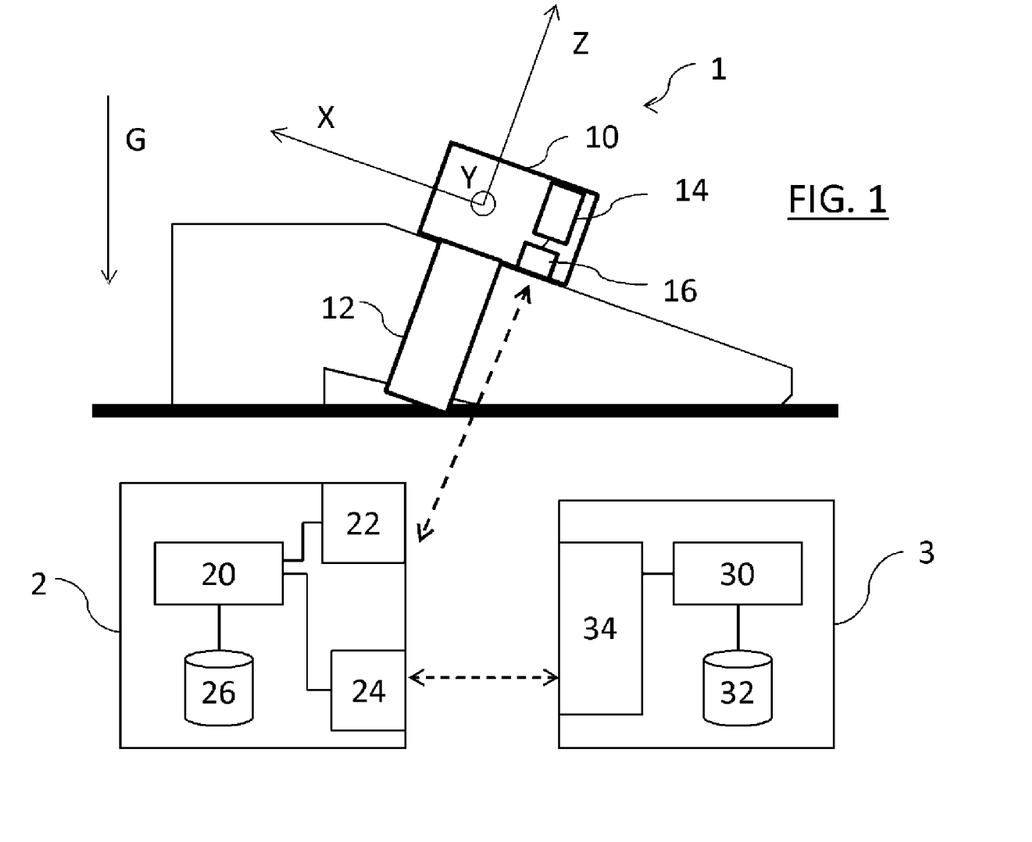
FIG. 1 schematically illustrates a system for characterizing gait and the foot of a subject seen in profile.

In reference to FIG. 1, a system for characterizing gait comprises a measuring device 1, a signal processing device 2 and a server 3.

The measuring device 1 comprises at least one motion sensor 10 and a belt 12.

The belt 12 is adapted to be attached around the foot of a subject, for example between the heel and the toes as shown in FIG. 1. The motion sensors 10 are fixed to the belt 12 so as not to impair the walking of the foot to which the belt 12 is attached.

For example, the measuring device 1 provides three motion sensors 10 for measuring motions of the foot along three axes X, Y and Z together defining a measuring marker attached to the device 1.

For example, at least one angular speed sensor is used around one of the above axes and/or at least one acceleration sensor along one of the above axes.

The measuring device can also comprise at least one magnetometer. For example, three magnetometers are provided, each magnetometer being configured to acquire a magnetic field component along one of the respective axes X, Y, Z.

The measuring device 1 also comprises internal signal processing means 14, and a communications interface 16.

The signal processing means 14 are configured to develop at least one output motion signal from at least one of the elementary signals delivered by each of the different motion sensors.

The communications interface 16 is configured to communicate with the signal processing device 2. The communications interface is especially capable of transmitting to the signal processing device 2 each output signal produced by the internal processing means of the measuring device 1.

The communications interface 16 is preferably wireless so as not to impair the walking of the subject when the measuring device 1 is attached to his foot.

In an embodiment, the measuring device 1 is a device marketed by the company Xsens and is fixed to a foot by way of Velcro tape, and the output signals are sampled at 100 Hz.

The signal processing device 2 comprises at least one processor 20, a first communications interface 22, a second communications interface 24 and an internal memory 26.

The processor 20 is configured to implement a method for characterizing gait coded in the form of program code instructions, on the basis of signals received via the two communications interfaces 22 and 24.

The communications interface 22 is adapted to receive the output signals emitted by the measuring device 1, for example by means of Wi-Fi protocol or Bluetooth protocol.

The communications interface 24 is adapted to communicate with the remote server 3, via a public network such as the Internet.

The signal processing device 2 can for example be in the form of a mobile terminal, of a portable computer, or a PC.

The server 3 comprises a communications interface 34 for communicating with the signal processing device 2, a processor 30 and a memory 32 adapted to store a set of measuring signals, and data adjacent to these signals, in the form of a database.

The steps of a method for characterizing gait implemented by means of the system of FIG. 1 will now be detailed.

Preliminary Phase for Collection of Reference Signals

Figure 2:
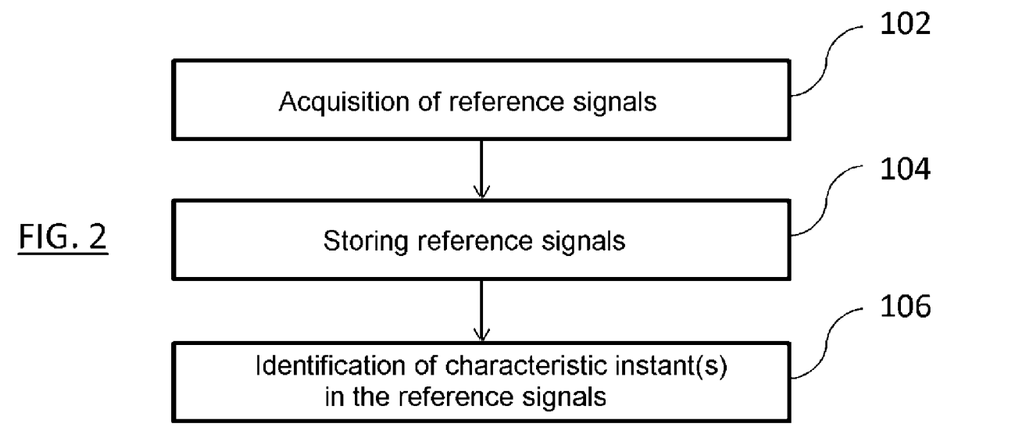
FIG. 2 is a flowchart of steps of a preliminary phase to a method for characterizing gait, according to an embodiment of the invention.

In reference to FIG. 2, a preliminary phase for collection of reference signals is carried out.

In a first step 102 of this preliminary phase, each reference signal is measured on a reference subject.

Acquisition 102 of a signal is performed by means of the acquisition system illustrated in FIGS. 1 and 2. To this end, a measuring device 1 is attached to a foot of a reference subject (or even two devices 1, one for the left foot and the other for the right foot). The reference subject is then invited to walk according to a predetermine clinical protocol.

While the reference subject is walking, the motion sensors 10 acquire signals representative of a motion parameter (acceleration and/or speed, for example angular speed) of the foot along the axes X, Y, Z, which are then processed by the internal processing means of the measuring device 1 to generate at least one reference acceleration signal of the corresponding foot of the reference subject.

The internal processing means can also use the measurements of magnetic fields acquired by the magnetometers, if present in the measuring devices 1.

Each one of the two measuring devices 1 (left and right feet) acquires nine raw signals (3D accelerations, 3D angular speeds and magnetic fields 3D) in the marker linked to the sensor defined by the axes X, Y and Z, these signals optionally able to be recalibrated or calibrated in a fixed marker relative to the ground via the internal processing means 14 of the measuring devices 1, to obtain the reference signals.

Some of the components pertinent for characterizing a gait are preferably used as reference signals. Three pertinent components for characterizing the gait shown in FIG. 1 are:
- an acceleration signal of the reference subject measured in a direction G normal to the ground,
- an acceleration signal of the reference subject measured along the axis Z linked to the device 1, which axis is normal to the upper surface of a foot of the reference subject,
- an angular speed signal of rotation of a foot of the reference subject around the axis Y during walking in a straight line by the reference subject (this axis Y being perpendicular to the axis Z and parallel to an axis of inclination of the foot in the region of the ankle).

Each reference signal is then transmitted to the processing device 2 via the interface 22, then to the server 3 via the interfaces 24 and 30.

In a step 104, the measured reference signal is stored in the memory 32 of the server 3. A reference signal can be stored in the internal memory 26 of the processing device 2, in place of or in addition to the memory 32 of the remote server 3.

In a step 106, each stored reference signal forms the object of an annotation aiming to determine at least one marker instant characteristic of the step of the reference subject.

This annotation step can be conducted empirically by a practitioner who scrutinizes the reference subject's gait during acquisition 102 of the reference signal.

Also, at least one information characteristic of the corresponding reference subject, previously determined, can be associated with each reference signal.

An information characteristic of gait can for example identify a particular class of subject, among several predetermined classes.

A class can relate to a type of gait (normal, limp, . . . ), severity of the gait affliction, a gait speed, the age of the reference subject (young, elderly, . . . ), etc.

For example, this information can relate to a complaint expressed by subjects (sensorial, motor, equilibrium, cognitive or hearing conditions, vertigo, dizziness or pain), to a confirmed and characterized deficit (lateralization, chronic or acute occurrence) of the subject (proprioceptive, vestibular, visual, motor: hemiparesis, paraparesis, Parkinson's disease . . . ). This information can include the anatomical level of the lesion: central or peripheral nervous system or in the sensorial organs (central vestibule, peripheral vestibule, peripheral nerves, spinal cord, torso, cerebellum, articulation of lower members, cerebral Hemisphere: cortex, ganglions of the base or of the white matter). This information can also refer to the etiology of the disorder (vascular, inflammation, traumatism, infection, tumor before or after surgery, degenerative, toxic, metabolic, psychosomatic . . . ).

The same steps 102, 104, 106 are implemented in an iterative manner for several reference subjects.

On completion of the preliminary phase, a plurality of reference signals is stored in the memory 32 and each reference signal is annotated with at least one characteristic instant of the step of the reference subject on which the reference signal has been measured, and/or at least one information characteristic of the reference subject.

It is possible to store a signal whereof the duration covers at least one part of a step or several steps of the corresponding reference subject.

All the same, it is preferable to store a reference signal having a duration which covers at least part of a single and one-only step of the reference subject so as to limit memory consumption by the reference signal and avoid potential information redundancy. The or each characteristic instant stored in addition to the reference signal itself relates to this single step.

Also, the use of a single and one-only step of the reference subject or of part of this step increases the sensitivity and specificity of this method. Also, it enables better results when the step of the target subject has a non-conventional form.

The use of at least part of a single and one-only step of the reference subject corresponds for example to use of a few or several phases of the step such as the support phase, initial contact, swaying. . . .

In practice, this annotation is embodied by storing data for locating the characteristic instants in the corresponding reference signal, these data being linked logically to this reference signal in the memory 32 or 26.

The reference subjects in which the acceleration reference signals are measured preferably have different gait profiles. In general, the reference subjects in which the acceleration reference signals are measured can be healthy subjects or patients (subject afflicted by a medical disorder).

Figure 3A:
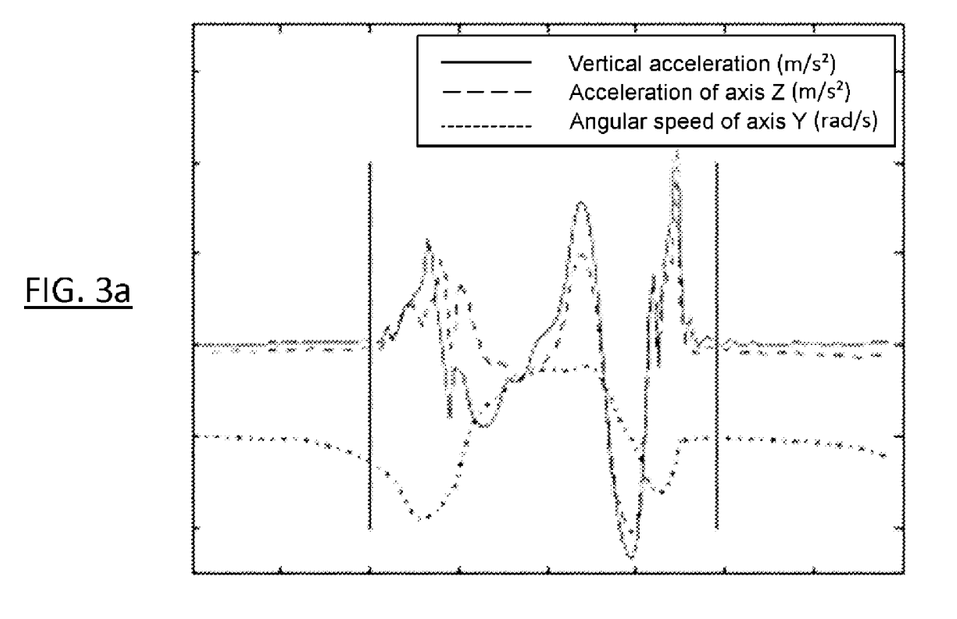
FIGS. 3a and 3b illustrate two measuring signals acquired by implementing the preliminary phase of FIG. 3.
Figure 3B:
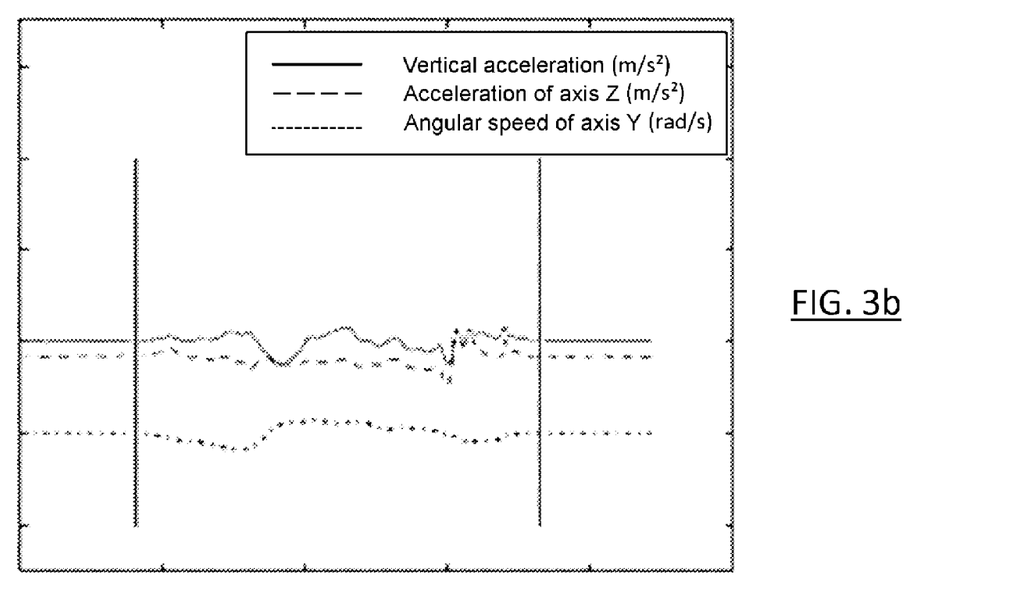

For example,
- at least one of the reference signals is measured on a subject afflicted with gait disorder (three examples of reference signals measured on a patient afflicted with a hip problem are illustrated in FIG. 3*b*); and
- at least one of the reference signals is measured on a healthy subject, i.e., a subject who is not afflicted with gait disorders (such as the three reference signals shown in FIG. 3*a*).

In this way, the invention also refers to a method for collecting information on the gait such as the style of walking or any pathology. So, it is possible for example to distinguish slight lameness, particular ways of lifting the foot, bowed legs, swaying when walking. Even if a common structure can optionally be detected between the reference signals shown in FIGS. 3a and 3b, it should be noted that their amplitudes are very different (in FIG. 3b, the subject in fact tends to drag his feet, which modifies the structure and amplitude of the step comparatively to the reference subject of FIG. 3a).

Also, the different reference signals collected are not necessarily of the same duration or associated with an identical number of characteristic instants of steps. It is actually understood that, from one reference subject to the other, a step can have a different duration.

The collected reference signals thus constitute a library of steps covering a wide range of gaits, to be used for characterizing the step of a qualified subject below as "target" subject, this target subject preferably being different to the reference subjects.

Gait Characterization Phase of the Target Subject

Figure 4:
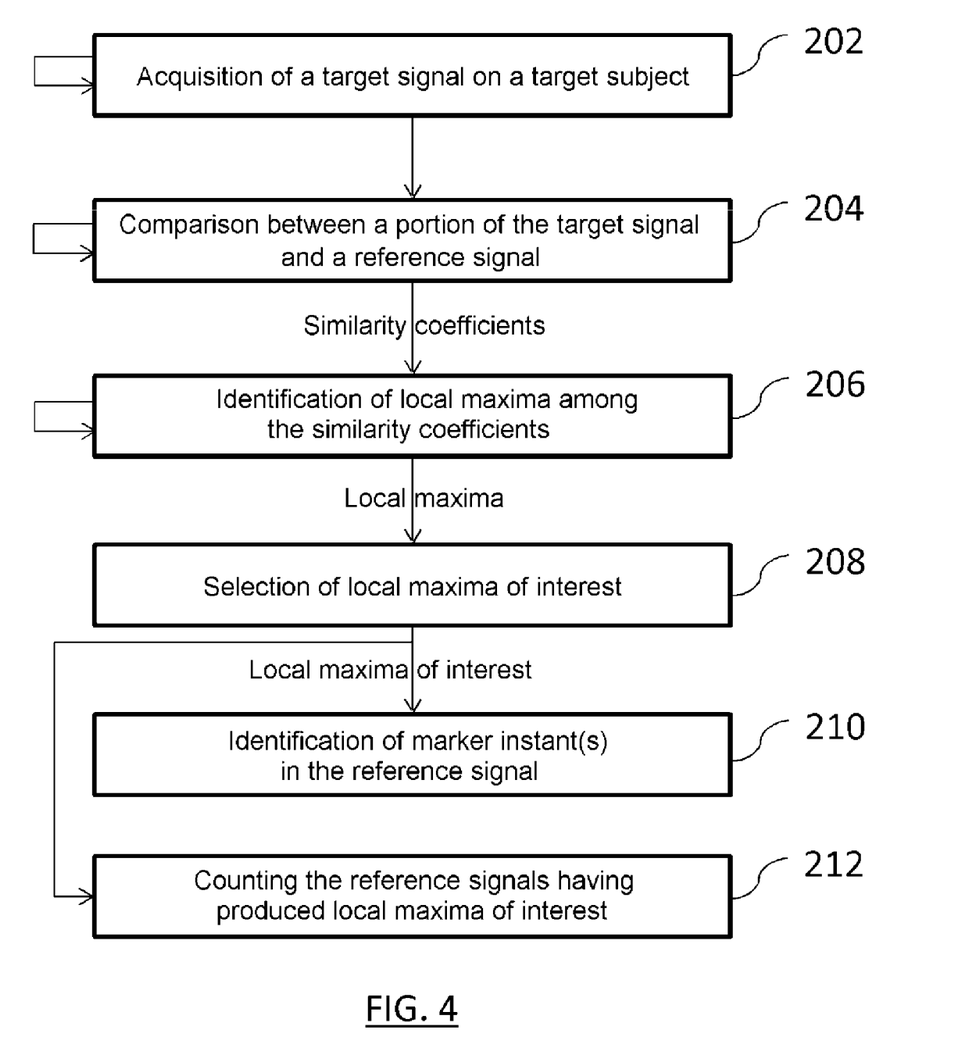
FIG. 4 is a flowchart of steps of a method for characterizing gait according to an embodiment of the invention.

In reference to FIG. 4, a method for characterizing gait of the target subject comprises the following steps.

In a step 202, the measuring device 1, previously fixed to a foot of the target subject, acquires at least one motion signal of the target subject, this signal being qualified below as "target signal".

The method according to the invention can be implemented on a target signal having been previously measured.

A target signal is for example an acceleration signal of the foot along the axis X, Y and/or Z, or a signal of angular speed of the foot around the axis X, Y and/or Z.

The target signal and the reference signals are therefore measured on different subjects. To improve detection, the acquisition protocol of the reference signals is representative of the conditions in which the target signal is generated.

The target signal is then transmitted to the processing device 2.

In a step 204, comparison between the target signal and a reference signal is carried out.

This comparison 204 can be performed by the processor 20 of the processing device 1; in this case, the processing device 1 sends a request to the server 3 for downloading a reference signal in light of this comparison 204. As a variant, the comparison 204 is performed by the server 3, the processing device then serving only as transmission relay of the target signal between the measuring device 1 and the server 3.

The comparison 204 is more precisely performed for different temporal portions of the target signal shifted temporarily relative to each other in the target signal. It is understood that as many comparisons are made as temporal portions defined in the target signal.

Each temporal portion of the target signal has the same duration T as the reference signal to which this portion will be compared.

The different portions of the target signal can be shifted relative to each other by a constant temporal step.

The different portions of the target signal can overlap.

The comparison 204 of a given temporal portion of the target signal with a reference signal produces a coefficient representative of a similarity probability between the two compared signals, this coefficient being called "similarity coefficient" below.

The comparison 204 comprises for example a correlation of the temporal portion of the target signal with the reference signal; in this case, the similarity coefficient depends on the Pearson linear coefficient between the two correlated signals.

The similarity coefficient p(x,y) between two signals x and y can more precisely be expressed as the absolute value of the Pearson linear coefficient, as follows:

$$\rho(x, y) = \frac{|\mathrm{cov}(x, y)|}{std(x)std(y)}$$

where cov(x, y) designates the covariance of these signals x and y, std(x) and std(y) designate the respective standard deviations of the signals x and y.

In this case, a high value of similarity coefficient will indicate strong similarity between the temporal portion of the target signal and the compared reference signal. Yet, a low value of this similarity coefficient will indicate a low similarity between the two compared signals.

For N temporal portions of the target signal, N similarity coefficients are therefore produced, each having a specific value via N comparisons 204. The N comparisons made scan the entire duration of the target signal.

The set of N similarity coefficients produced from the target signal and of a same given reference signal is called coefficient sequence hereinbelow.

The coefficients of a sequence are classified by order of temporal position of N different temporal portions of the target signal considered during comparison step 204. A running direction of a coefficient sequence therefore corresponds to a temporal running direction of the target signal.

The comparison step 204 is repeated for each reference signal previously stored during the preliminary phase. It will be evident that since each reference signal is of a duration T potentially separate from that of the others, the temporal portions of the target signal which are compared to it can be also redefined differently for each reference signal.

By crossing each reference signal with the target signal, the total number of sequences of similarity coefficients produced on completion of these repetitions is equal to the number of target signals acquired simultaneously on the target subject, multiplied by the number of stored reference signals.

Each sequence can have a number of different coefficients, as a function of the step selected to shift the temporal portions relative to each other in the corresponding target signal, and as a function of the length (duration) of the relevant reference signal.

In a step 206, the processor performs identification of local maxima in a given sequence of similarity coefficients.

In a given sequence, a current coefficient constitutes a local maximum if the following coefficient in the sequence and the preceding coefficient in the sequence have values which are less than that of the current coefficient. The detection of local maxima typically proceeds via a series of comparisons between values of adjacent coefficients in a sequence.

Each local maximum is a similarity coefficient produced from a portion of the signal which more resembles the reference signal than the adjacent portions of the target signal.

A given sequence may thus comprise zero, one or more local maxima.

Step 206 is repeated for each coefficient sequence produced.

In a selection step 208, the processor selects, from several identified local maxima, some local maxima of interest.

The local maxima of interest are selected on the basis of the value of the similarity coefficients: a local maximum is not selected as local maximum of interest if its value is less than a predetermined threshold A, so as to eliminate local maxima having low values of similarity probability.

For example, in the case of similarity coefficients defined as the absolute value of Pearson linear coefficients, only the local maxima having a value greater than or equal to 0.5 are retained as local maxima of interest.

The predetermined threshold A is preferably between 0.6 and 0.8.

The selection 208 can be advantageously performed by decreasing order of value of the similarity coefficients; in this way, the number of comparisons with the threshold A is reduced.

Another selection criterion 208 of a local maximum is the overlapping of the corresponding portion of the target signal with the temporal portion of the same target signal from which another similarity coefficient has been produced, constituting not only another local maximum, and also having already been selected as local maximum of interest among the local maxima of the sequence.

In other words, given that a first local maximum is produced from comparison between a first portion of the target signal and a reference signal, then selected as local maximum of interest,
- a second local maximum produced from a comparison between the reference signal and a second portion which overlaps the first portion is not selected as local maximum of interest, and
- a third local maximum produced from comparison between the reference signal and a third portion which does not overlap the first portion is selected as local maximum of interest.

The selection step 208 of the local maxima of interest is preferably performed by order of decreasing value of coefficient value; it is certain that the local maxima having the biggest values in the sequence will be selected as local maximum of interest.

To the extent where as many sequences as reference signals can be produced, the order of selection 208 can be made after sorting of all the local maxima documented in all the sequences.

On completion of the selection step 208, there is at least one local maximum of interest, which is associated with a specific portion of the target signal; and when a plurality of local maxima of interests is produced, it is certain that the specific portions of the associated target signal are temporarily separated in the target signal (i.e., do not overlap).

In an identification step 210, the processor identifies in the target signal at least one characteristic instant of a step of the target subject on the basis of the selected local maximum or maxima of interest.

This identification step 210 comprises downloading from the server 3 to the processing device 2, of the characteristic instant marker(s) annotated in the reference signal considered here, during the preliminary phase for collection of the reference signals. As a variant, the identification step is performed by the server 3.

A marker instant characteristic of the target subject is identified in the target signal by examining a local maximum of interest selected in step 208.

As recall, the reference signal having resulted in achieving a given local maximum of interest has been annotated with at least one characteristic instant during the preliminary phase and/or with at least one characteristic of the corresponding reference subject.

Figure 5:
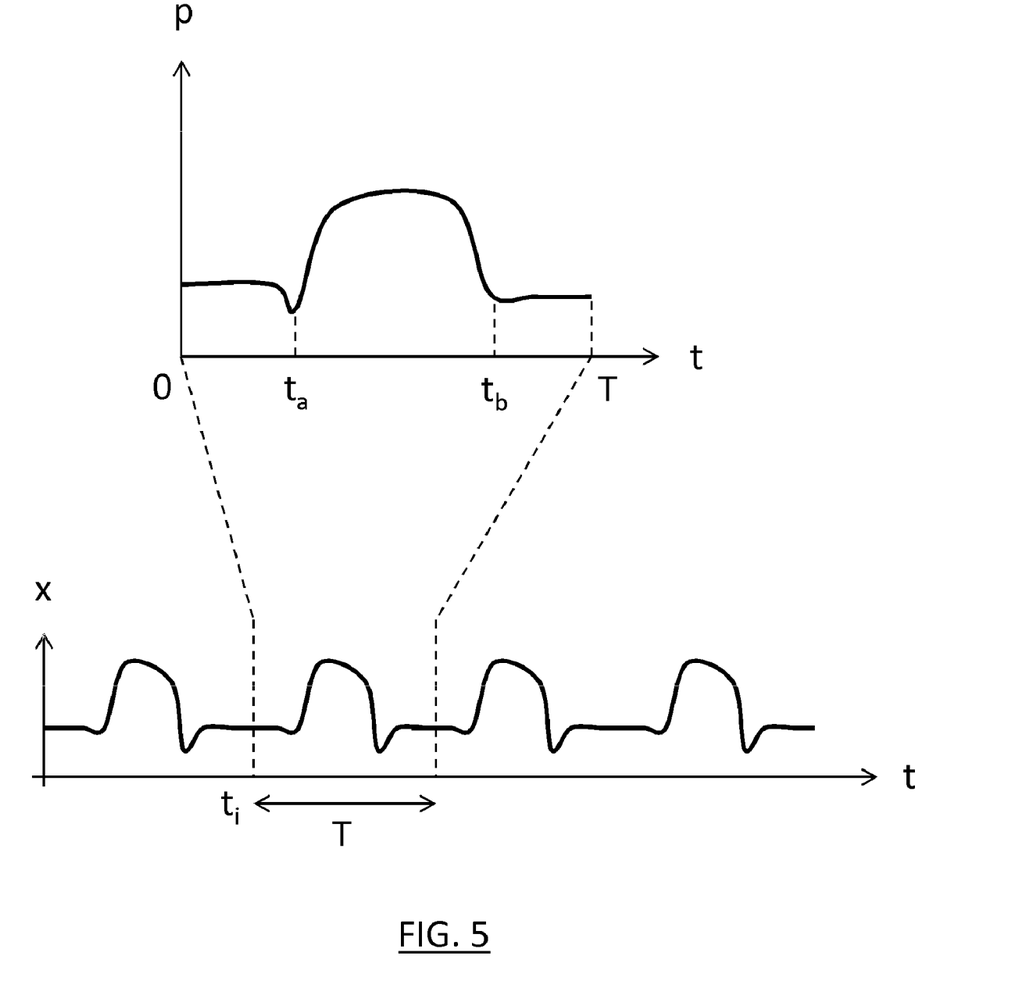
FIG. 5 illustrates a reference signal and a target signal compared during implementation of the detection method of FIG. 4.

FIG. 5 for example shows a reference signal p comprising two characteristic instants: a start of step instant $t_a$ and an end of step instant $t_b$.

The characteristic instant $t_a$ is deferred in the temporal portion of the target signal to the temporal position $t_i+t_a$, where $t_i$ designates the start instant of the temporal portion in the target signal.

Similarly, the characteristic instant $t_b$ is deferred in the temporal portion of the target signal to the temporal position $t_i+t_a$, where $t_i$ designates the start instant of the temporal portion in the target signal.

Each marker instant predetermined during the preliminary phase thus is traced in the target signal.

The processor 20 proceeds in the same way for any other selected local maximum of interest.

In a particular application the identification step 210 thus counts the steps of the target subject.

In an embodiment, identification 210 of characteristic marker instant(s) is not necessarily carried out for all the local maxima selected during selection step 208. For each local maximum of interest, in this case the processor calculates a ratio between dimensional characteristics of the two compared signals on the basis of which the maxima have been identified 206, then selected 208.

If this dimension ratio exceeds a predetermined threshold p, then identification step 210 of characteristic instant is not taken in the temporal portion of the target signal.

For example, if the numerator of the ratio is the dimensional characteristic relating to the target signal and if the denominator of the ratio is the dimensional characteristic relating to a reference signal, it is verified whether the ratio is under the threshold μ, and if this is the case, the identification step 210 of characteristic instant is not taken in the temporal portion of the target signal.

If not, the identification step 210 according to the preceding modalities is conducted on this temporal portion of the target signal.

The dimension ratio can be for example an amplitude ratio between the compared signals or a variance ratio between the compared signals.

Several ratios can be calculated for a pair of compared signals; it can be provided to not initiate the identification step of marker instant if at least one of the ratios is greater than a predefined threshold.

Calculation of the dimension ratios is preferably carried out after the identification 206 of the local maxima, most preferably after the selection of the local maxima of interest, so as to limit the number of ratios to be calculated.

Steps 202, 204, 206, 208 and 210 can be repeated for several target signals acquired simultaneously via different sensors of the measuring device 1 (for example acceleration signals along different axes among those mentioned above).

Instances of processing other than the identification step 210 can be performed once local maxima have been selected in the selection step 208.

The processor 20 can for example count 212 the number of times a reference signal has generated a local maximum of reference interest.

The processor 20 then downloads the information characteristic of the reference subjects (accounted for during the preliminary phase) which are associated with the reference signals having generated at least one of the local maxima of interest.

The processor 20 can for example calculate a representation percentage of each characteristic information in the set of the local maxima of interest and therefore of the target signal.

It is quite possible that a reference signal (or several reference signals carrying the same gait characteristic information) is represented as a majority in the local maxima of interests.

The majority characteristic information can be attributed to the target subject.

For each class of reference signals generated from information characteristic of the reference subjects, the processor 20 can also count 212 the number of local maximum of interest linked to this class and therefore having been associated with the target signal.

The processor 20 can then for example calculate a representation percentage of each characteristic information in the target signal.

The majority characteristic information can be attributed to the target subject.

Example of Algorithmic Implementation of the Detection Method

The detection method can be implemented in the form of a computer program comprising code instructions capable of being executed by the processor 20.

An algorithm consisting of a possible embodiment of this computer program will be detailed below.

It is considered below that the measuring device 1 supplies a k-tuple of discrete signals measured on a same subject. This k-tuple can be represented by a vector of length |p| and dimension k.

The following notations are introduced:

x is a vector representative of a k-tuple of discrete target signals measured on the target subject.

p is a vector representative of a k-tuple of discrete reference signals measured on the same reference subject.

|P| is the number of vectors p.

|x| (respectively |p|) is the length of the vector x (respectively p), counted as number of samples.

$x^{(k)}$ (respectively $p^{(k)}$) is the $k^{th}$ component of the vector x.

$x_{i,j}^{(k)}$ is the temporal portion of x(k) between the samples of indices i and j; there is therefore $x_{1:|x|}^{(k)}=x^{(k)}$.

The similarity coefficients, noted r, are calculated between the reference signals and the target signal during comparison step 204, for all the possible temporal portions of length |p|, making a total of 3×|P|×|x| similarity coefficients:

$$\forall k, \forall p \in P, \forall 1 \leq x \leq |x|$$

$$r(k,p,i)=\rho(p^{(k)},x_{i:i+|p|-1}^{(k)})$$

where r(k, p, i) is the similarity coefficient coming from the comparison between the $k^{th}$ component of the reference signal p and the $k^{th}$ component of the target signal at the instant i, and where ρ is a Pearson linear coefficient as absolute value.

During step 206, a coefficient r(k, p, i) is designated as being a local maximum if it is greater than its direct temporal neighbors. The set L of local maxima is therefore the set of the similarity coefficients r(k, p, i) cumulatively verifying the following two conditions:

$$r(k,p,i)>r(k,p,i-1)$$

$$r(k,p,i)>r(k,p,i+1)$$

The set L contains all the positions acceptable for steps of the target subject; each coefficient r(k, p, i) can be interpreted as the likelihood of finding, in the target signal at the instant i, a step similar to that of the reference signal of index p.

The selection step 208 is coded in the manner of a greedy process. With each iteration of the algorithm, the biggest coefficient value r(k*,p*,i*) in the set L is selected:

If the step p* positioned at the instant i* overlaps a step which has already been detected, it is rejected and the process is restarted;

If the step p* can be positioned at the instant i* without overlapping the preceding detections, it is considered as detected and the indices between i* and i*+|p*|−1 are prohibited in the next iterations.

The greedy algorithm of selection step 208 ends when all indices are prohibited, or when all the local maxima of the set L have been considered, or when the values of the coefficients remaining in the set L are all smaller than the predetermined threshold A. This threshold A acts as an acceleration parameter of the algorithm; this actually prevents rotating the algorithm too long.

The greedy algorithm of step 208 produces a set S of local maxima of interests.

The identification step 210 of the characteristic instants is then conducted on the basis of this set S and the threshold p. As indicated earlier, the threshold p is used to reject some characteristic instants, in case of excessive dimensional gap between a portion of the target signal and a portion of reference signal associated with a local maximum of interest included in the set S.

For example, the predetermined threshold p is less than or equal to 0.2 and is preferably between 0.05 and 0.2, more preferably between 0.1 and 0.2.

Results

The inventors were able to achieve particularly satisfactory results after setting up a database of signals containing 295 signals measured in 74 subjects including 23 healthy and 51 suffering from a variety of orthopedic disorders of the knee, the hip or the ankle, some of the subjects having gone through the protocol several times.

The clinical acquisition protocol of the reference signals, to which the reference subjects wearing the measuring device 1 were subjected is the following:

remain immobile for 6 seconds, walk fully upright for 10 meters at a comfortable pace, make a U-turn, return to the start point, remain immobile for 2 seconds.

All signals of the database have been annotated manually with two characteristic marker instants:

a start of step instant $t_a$, at which the heel lifts off the ground, an end of step instant $t_b$, at which the toes are resting on the ground and stabilized.

In total, 9357 steps have been stored (4674 on the right foot and 4683 on the left foot).

Operation of the detection method has been tested by way of the following evaluation method.

|P| steps in the database which constitute a learning base were selected randomly.

Steps in the database constituting a test base were also selected.

To prevent overlearning, all the signals measured on subjects present in the learning base are discarded from the test base.

The method for characterizing gait was applied to each signal of the test base by using the |P| signals of the learning base as reference signals.

A precision score and a recall score of the start and end of step characteristic instants identified in each signal of the test base were then calculated by application of the method according to the invention, given that a step is correct if the average of the detected start and end of step instants falls to an instant where a step is effectively present in light of the annotations collected by practitioners during the preliminary collection phase described earlier.

The precision and recall scores for all the signals of the test base were then averaged.

In the results presented below, this method has been repeated 100 times and focus was on the average and the standard deviation of precision and recall scores.

Table 1 below presents the precisions and recalls (average, and standard deviation in parentheses on 100 simulations) for different numbers of |P| of reference signals.

TABLE 1

| Value of |P| | Precision | Recall |
| --- | --- | --- |
| 5 | 96.6 (5.04) | 96.6 (1.04) |
| 10 | 96.1 (3.76) | 96.5 (3.42) |
| 15 | 95.7 (3.73) | 96.4 (3.25) |
| 20 | 96.0 (2.81) | 97.0 (1.76) |
| 25 | 95.8 (2.67) | 97.0 (1.43) |

The threshold $\lambda$ has been fixed at 0.6 to reduce calculation time. The first observation is that all these scores seem fairly similar: all the average scores are between 95% and 97%, even when just 5 reference signals are used. All standard deviations are smaller than 5%, suggesting major stability of the method.

If the number of reference signals does not seem to significantly affect average performances, it mainly influences the robustness of the method. It is evident that the more the number of reference signals increases, the more the standard deviations decrease, and therefore the more robust the method. This observation makes sense as it is intuitive that the more reference signals there are, the greater chance that all pathologies and types of steps are considered, which tends to uniformize the results for all the signals of the test base. When |P|=5, this shows an asymmetry between the standard deviations of precision and recall. Due to the low number of reference signals, the correspondence between pathological steps of small size and healthy steps of larger size is forced, which can cause oversensing and tends to drop precision.

Table 2 hereinbelow presents the precisions and recalls (average, and standard deviation in parentheses of 100 simulations) for different values of the predetermined threshold $\lambda$.

TABLE 2

| Value of $\lambda$ | Precision | Recall |
| --- | --- | --- |
| 0.60 | 95.23 (4.50) | 97.63 (1.61) |
| 0.65 | 93.97 (7.52) | 96.74 (4.58) |
| 0.70 | 95.96 (4.96) | 97.33 (3.22) |
| 0.75 | 96.44 (4.32) | 97.19 (1.99) |
| 0.80 | 97.03 (1.02) | 96.59 (1.89) |
| 0.85 | 97.83 (2.92) | 95.26 (1.93) |
| 0.90 | 98.49 (4.74) | 90.36 (2.51) |

When the predetermined threshold $\lambda$ increases, only the reference signals which are highly correlated to the models are selected: this increases the precision. On the contrary, when the predetermined threshold $\lambda$ decreases, the recall increases and the precision decreases. These results confirm the utility of the parameter $\lambda$:$\lambda$ by increasing to an appropriate value (of the order of 0.6 to 0.8), it is possible to increase the precision (and to the robustness of the precision) while retaining the recall constant. Also, $\lambda$ has an incidence on the calculation cost. For example, using $\lambda$=0.8 instead of $\lambda$=0 (equivalent to the algorithm without $\lambda$) it is possible to calculate the result around twice faster. It is therefore interesting to use the possible biggest value of $\lambda$. The best performances are obtained for $\lambda$=0.8, which constitutes a good compromise between the recall and the precision.

Table 3 hereinbelow presents the precisions and recalls (average, and standard deviation in parentheses of 100 simulations) for different values of the predetermined threshold $\mu$.

TABLE 3

| Value of $\mu$ | Precision | Recall |
| --- | --- | --- |
| 0.05 | 96.23 (2.29) | 97.42 (0.93) |
| 0.10 | 95.92 (5.66) | 97.04 (1.60) |
| 0.15 | 97.03 (4.02) | 96.59 (1.89) |
| 0.20 | 96.72 (6.30) | 95.78 (1.89) |
| 0.25 | 97.68 (2.67) | 95.25 (1.31) |
| 0.30 | 97.84 (4.94) | 93.88 (2.73) |

The parameter $\mu$ mainly influences the recall. In fact, when $\mu$ is too big, all the measurements whereof the amplitude is too different to that of the reference signals are not considered. This has a double effect: if one of the reference signals corresponds to a pathological patient whereof the steps have a narrow amplitude, it will not be able to detect measurements on patients in good health. The reverse situation can also occur. In fact, when $\mu$ increases, the normalization effect provided by the Pearson correlation coefficient is neutralized. Table 3 shows that $\mu$ should preferably not be greater than 0.2 such that the recall is not too low.

This step, based on 100 simulations, has resulted in testing 21000 different configurations. Of these configurations, it is possible to mention the configuration: |P|=5 reference signals, $\lambda$=0.75 and $\mu$=0.1, with an average recall of 98.40% and average precision of 98.44%. This choice of parameter is an example and the parameters could be modified as a function of the content of the database of steps and sequences to be analyzed.

Good performances of the method according to the invention are linked to the reference signals which make up the library. It is remarkable that this method needs only a small number of reference signals, which tends to show that the algorithm does not need a large library to achieve accurately. For example, the optimized method comprises 5 reference signals: 1 reference signal belonging to a healthy subject, 3 reference signals corresponding to neurological disorders, and 1 reference signal associated with orthopedic conditions.

The method according to the invention further has the advantage of being capable of accurately detecting the limits of steps and adapting to different durations of steps. For 90% of steps, errors in starting, arrival and the time duration are under 0.25 seconds (as absolute value). These results are satisfactory relative to the annotations on uncertainty by experts and specialists.

The detection method according to the invention has been compared to a Pan-Tomkins preprocessing method cited in the introduction, configured with the parameters suggested in the article "Automatic step detection in the accelerometer signal", by H. Ying, C. Silex et al.

The results supplied by this former method are low-precision (of the order of 25.6% to 51.20% as a function of the groups of sequences used). Also, this method does not detect a characteristic instant of a step such as the present invention could do (e.g. start of step instant or end of step instant).

The Pan-Tomkins method has been optimized on the set of the database via the choice of optimum values for several parameters (e.g. fmin, fmax, integration window, the size of the quarter and the level of noise) so as to maximize the F-measurement. When optimized, the algorithm gives 97.82% of recall and a precision of 95.72%. The detailed results are presented in table 4. While these scores are comparable to the method according to the invention on healthy subjects, it should be noted that the Pan-Tomkins method has difficulty in treating subjects exhibiting disorders such as neurological or orthopedic disorders. In particular, on these subjects, oversensing occurs, reducing precision. This shows a limit in detection methods of classic steps based on processing the signal: if the signals to be studied have different properties (noise, frequential content, amplitudes), it is difficult to find a single processing solution adapted to all signals.

TABLE 4

|  | Invention | | Pan-Tomkins | |
| --- | --- | --- | --- | --- |
|  | Recall | Precision | Recall | Precision |
| Healthy subjects | 98.93 (2.22) | 98.98 (2.43) | 99.14 (1.71) | 97.09 (3.78) |
| Subjects with orthopedic disorders | 97.54 (2.92) | 98.77 (2.12) | 98.78 (2.09) | 94.87 (5.09) |
| Subjects with orthopedic disorders | 98.55 (3.05) | 98.05 (3.02) | 96.80 (3.52) | 95.49 (4.55) |
| Total | 98.40 (2.89) | 98.44 (2.72) | 97.82 (3.07) | 95.72 (4.56) |

Ultimately, the detection method implemented in accordance with the invention produces robust performance, even by using a small number of reference signals.

The detection method according to the invention can have multiple applications. The detection method can in particular serve as preliminary phase to diagnosis or prognosis of gait disorder. Given that it uses data having been measured previously, it needs no interaction with the target subject to be implemented.

The invention claimed is:

1. A method for characterizing gait comprising steps of:
receiving, by one or more processors, a target motion signal previously acquired from a target subject, wherein the target motion signal is representative of a motion of a foot of the target subject;
comparing, by the one or more processors, at least one portion of the target motion signal with a plurality of reference signals,
wherein at least one of the plurality of reference signals is compared to several portions temporally shifted relative to each other of the target motion signal, so as to produce a sequence of similarity coefficients ordered according to time positions of the several portions of the target motion signal,
wherein each of the similarity coefficients is representative of a similarity probability between the target motion signal and said at least one signal of the plurality of reference signals,
wherein the plurality of reference signals comprises:
at least one motion signal previously acquired from a reference subject afflicted by a gait disorder, and
at least one motion signal acquired from a healthy reference subject;
selecting, by the one or more processors, at least one local maximum value in the sequence of similarity coefficients;
selecting, by the one or more processors, data in the at least one of the plurality of reference signals, wherein the data is associated with the at least one local maximum value, and wherein the data comprises at least one of two predetermined marker instant characteristics of a step;
identifying, by the one or more processors, at least one of two marker instant characteristics of a step of the target subject in the target motion signal, using the selected data; and
outputting, by the one or more processors to a user, the identified at least one of two marker instant characteristics to be used in diagnosis or prognosis of gait disorder.

2. The method according to claim 1, comprising calculating, by the one or more processors, a ratio between a dimensional characteristics of the at least one of the plurality of reference signals and a dimensional characteristic of the target motion signal, and wherein identifying the at least one of two marker instant characteristics of a step of the target subject is not carried out whenever the ratio exceeds a predetermined threshold.

3. The method according to claim 1, further comprising counting, by the one or more processors, the number of selected local maximum values corresponding to a given reference signal.

4. The method according to claim 1, further comprising:
comparing a first similarity coefficient of the sequence of similarity coefficients and a second similarity coefficient preceding the first similarity coefficient in the sequence, so as to produce a first comparison result; and
comparing the first similarity coefficient and a third similarity coefficient following the first similarity coefficient in the sequence, so as to produce a second comparison result;
wherein
the first similarity coefficient of the sequence is selected as the at least one local maximum value depending on the first comparison result and on the second comparison result.

5. The method according to claim 1, wherein the sequence of similarity coefficients comprises a first local maximum produced from a first portion among the several portions and a second local maximum value produced from a second portion among the several portions, wherein selecting the at least one local maximum value in the sequence of similarity coefficients comprises selecting the first local maximum, then not selecting the second local maximum whenever the first portion and the second portion temporally overlap.

6. A system for characterizing gait, comprising:
a receiving interface configured for receiving a target motion signal previously acquired from a target subject, wherein the motion signal acquired from the target subject is representative of the motion of a foot of the target subject, and at least one processor configured to:
- compare the motion signal with a plurality of reference signals,
  - wherein each comparison of the motion signal with one of the plurality of reference signals produces a similarity coefficient representative of a similarity probability between the compared signals,
  - wherein at least one of the plurality of reference signals is compared to several portions temporally shifted relative to each other of the target motion signal, so as to produce a sequence of similarity coefficients ordered according to time positions of the several portions in the target motion signal, and
  - wherein the plurality of reference signals comprises at least one motion signal previously acquired from a reference subject afflicted by a gait disorder, and at least one motion signal previously acquired from a healthy reference subject;
- select at least one local maximum value in the sequence of similarity coefficients;
- select data in the at least one of the plurality of reference signals, wherein the data is associated with the at least one local maximum value;
- identify at least one of two marker instant characteristics of a step of the target subject in the target motion signal, using the selected data; and
- output the identified at least one of two marker instant characteristics to be used in diagnosis or prognosis of gait disorder.

* * * * *